US010201491B2

(12) United States Patent
Garre Venkata Raghavendra et al.

(10) Patent No.: US 10,201,491 B2
(45) Date of Patent: Feb. 12, 2019

(54) POLYELECTROLYTE DENTAL ADHESIVES FOR WHITENING TEETH AND TEETH COMPONENTS

(71) Applicant: SafeWhite, Inc., Columbus, OH (US)

(72) Inventors: Satish Kumar Garre Venkata Raghavendra, Dublin, OH (US); Gary Fred Musso, Hopkinton, MA (US); Caitlin Marie Kiracofe, Columbus, OH (US); Ada Alicia Sierraalta, Columbus, OH (US); Michelle Anne Hurtubise, Kettering, OH (US); Carlos Eduardo Martinez, Cincinnati, OH (US); Deepti Gupta, Centerville, OH (US)

(73) Assignee: SafeWhite, Inc., Columbus, OH (US)

(*) Notice: Subject to any disclaimer, the term of this patent is extended or adjusted under 35 U.S.C. 154(b) by 0 days.

(21) Appl. No.: 15/920,154

(22) Filed: Mar. 13, 2018

(65) Prior Publication Data

US 2018/0360726 A1    Dec. 20, 2018

Related U.S. Application Data

(63) Continuation of application No. 15/473,355, filed on Mar. 29, 2017, now Pat. No. 9,937,120.

(60) Provisional application No. 62/314,798, filed on Mar. 29, 2016.

(51) Int. Cl.
| | | |
|---|---|---|
| *A61K 8/24* | (2006.01) |
| *A61K 8/25* | (2006.01) |
| *A61K 8/27* | (2006.01) |
| *A61K 8/29* | (2006.01) |
| *A61K 8/55* | (2006.01) |
| *A61K 8/64* | (2006.01) |
| *A61K 8/81* | (2006.01) |
| *A61K 8/84* | (2006.01) |
| *A61K 8/88* | (2006.01) |
| *A61Q 11/00* | (2006.01) |

(52) U.S. Cl.
CPC .............. *A61K 8/817* (2013.01); *A61K 8/24* (2013.01); *A61K 8/25* (2013.01); *A61K 8/27* (2013.01); *A61K 8/29* (2013.01); *A61K 8/55* (2013.01); *A61K 8/64* (2013.01); *A61K 8/84* (2013.01); *A61K 8/88* (2013.01); *A61Q 11/00* (2013.01); *A61K 2800/20* (2013.01)

(58) Field of Classification Search
CPC .............. A61K 7/16; A61K 7/18; A61K 7/22
USPC ........................................................ 424/49
See application file for complete search history.

(56) References Cited

U.S. PATENT DOCUMENTS

| | | |
|---|---|---|
| 4,137,303 A | 1/1979 | Gaffar et al. |
| 4,913,895 A | 4/1990 | Miyake et al. |
| 5,373,052 A | 12/1994 | Fukuda et al. |
| 6,004,567 A | 12/1999 | Marchi-Lehmann et al. |
| 6,719,834 B1 | 4/2004 | Braun et al. |
| 8,568,698 B2 | 10/2013 | Bridgeman et al. |
| 8,784,783 B2 | 7/2014 | Bridgeman et al. |
| 8,853,338 B2 | 10/2014 | Wang et al. |
| 9,814,778 B2 | 11/2017 | Lapitsky et al. |
| 9,937,120 B2 | 4/2018 | Venkata et al. |
| 2005/0002876 A1 | 1/2005 | Yukl et al. |
| 2006/0142411 A1 | 6/2006 | Ibrahim et al. |
| 2008/0118447 A1 | 5/2008 | Nathoo |
| 2009/0238778 A1 | 9/2009 | Mordas et al. |
| 2010/0104519 A1 | 4/2010 | Chung et al. |
| 2012/0045400 A1 | 2/2012 | Nowak |
| 2013/0022555 A1 | 1/2013 | Bridgeman et al. |
| 2013/0189313 A1 | 7/2013 | Stewart et al. |
| 2014/0271500 A1 | 9/2014 | Brody |

FOREIGN PATENT DOCUMENTS

| | | |
|---|---|---|
| WO | WO 2002/092049 | 11/2002 |
| WO | WO 2004/100884 | 11/2004 |
| WO | WO 2006/069236 | 6/2006 |
| WO | WO 2006/121610 | 11/2006 |
| WO | WO 2007/066837 | 6/2007 |
| WO | WO 2007/111616 | 10/2007 |
| WO | WO 2008/041055 | 4/2008 |
| WO | WO 2012/065148 | 5/2012 |

OTHER PUBLICATIONS

Ajun et al., "Preparation of aspirin and probucol in combination loaded chitosan nanoparticles and in vitro release study," *Carbohydrate Polymers.*, 75(4):566-574, Feb. 24, 2009.
Chemsol Korea. Nittobo's polyallylamines. Jan. 27, 2014. [Retrieved from the internet on Jun. 4, 2017]. <URL: http://www.chemsolkorea.com/eng/product/by-product.php?menujdx=9; p. 2, paragraphs 1-2.
Etienne et al., "Polyelectrolyte Multilayer Film Coating and Stability at the Surfaces of Oral Prosthesis Base Polymers: an in vitro and in vivo Study," *J Dent Res.*, 85(1):44-48, 2006.
Huang and Lapitsky, "Determining the Colloidal Behavior of Tonically Cross-Linked Polyelectrolytes with Isothermal Titration Calorimetry," *J Phys Chem B.*, 117:9548-9557, 2013.
Huang et al. "Salt-assisted mechanistic analysis of chitosan/tripolyphosphate micro- and nanogel formation," *Biomacromolecules.*, 13(11):3868-3876, 2012.

(Continued)

*Primary Examiner* — Walter E Webb

(74) *Attorney, Agent, or Firm* — Fish & Richardson P.C.

(57) ABSTRACT

This document relates to methods and materials involved in providing a tooth, tooth component, or inorganic dental material (e.g., a human tooth, a human tooth component, or an inorganic dental material within a human's mouth) with a white appearance. For example, a whitening adhesive containing a conjugate of at least a polyamine, a polyphosphate, and one or more whitening agents (e.g., titanium dioxide, zinc oxide, and/or hydroxyapetite) can be used to provide a tooth, tooth component, or inorganic dental material with a whiter appearance.

50 Claims, 9 Drawing Sheets

(56) References Cited

OTHER PUBLICATIONS

Huang et al., "Determining the Colloidal Behavior of Tonically Cross-Linked Polyelectrolytes with Isothermal Titration Calorimetry," *J Phys Chem B.*, 117(32):9548-9557, Aug. 15, 2013.

Huang et al., "Self-Assembly of Stiff, Adhesive and Self-Healing Gels from Common Polyelectrolytes," *Langmuir.*, 30:7771-7777, 2014.

International Search Report in International Application No. PCT/US2017/24807, dated Jun. 21, 2017, 18 pages.

Lamkin et al., "Temporal and compositional characteristics of salivary protein adsorption to hydroxyapatite," *J Dent Res.*, 75:803-808, 1996.

Lapitsky et al., "Ionically crosslinked polyelectrolyte nanocarriers: Recent advances and open problems," *Current Opinion in Colloid & Interface Science.*, 19(2):122-130, 2014.

Li et al., "Rheological properties of chitosan-tripolyphosphate complexes: From suspensions to microgels," *Carbohydrate Polymers.*, 87(2):1670-1677, Jan. 15, 2012.

Murthy et al., "Nanoparticle-Assembled Capsule Synthesis: Formation of Colloidal Polyamine—Salt Intermediates," *J Phys Chem B.*, 110(51):25619-25627, Dec. 28, 2006.

Paravina et al., "New shade guide for evaluation of tooth whitening—colorimetric study," *J Esthet Restor Dent.*, 19:276-283, 2007.

Park et al., "Infuence of fluorescent whitening agent on the fluorescent emission of resin composites," *Dental Materials.*, 23:731-735, 2007.

R.A. Witthous, "Text-Book of Chemistry: Inorganic and Organic with Toxicology." Seventh, Revised eddtion 1919; p. 301.

Raj et al., "Dependence of charge, sequence, hydrophobicity, hydrogen bonding potency and helical conformation for adsorption to hydroxyapatite and inhibition of mineralization," *J Biol Chem.*, 267:5968-5976, 1992.

Schilling et al., "Human safety review of "nano" titanium dioxide and zinc oxide," *Photochem Photobiol Sci.*, 9(4):495-509, Apr. 2010.

Shao et al., "A Water-Borne Adhesive Modeled after the Sandcastle Glue of P. californica," *Macromol Biosci.*, 9(5):464-471, May 13, 2009.

Shao et al., "Biomimetic Underwater Adhesives with Environmentally Triggered Setting Mechanisms," *Advanced Materials.*, 22(6):729-733, Feb. 9, 2010.

Shu et al., "A novel approach to prepare tripolyphosphate/chitosan complex beads for controlled release drug delivery," Int J Pharm., 201(1):51-58, May 15, 2000.

Stewart et al., Natural Underwater Adhesives, *J Polymer Sci Part B: Polymer Phy.*, 49:757-771, 2011.

Yu et al., "Synthesis of nanoparticle-assembled tin oxide/polymer microcapsules," *Chem Commun.*, 10:1097-1099, Mar. 14, 2006.

Zhang et al., "Design of Biocompatible Chitosan Microgels for Targeted pH-Mediated Intracellular Release of Cancer Therapeutics," *Biomacromolecules.*, 7(5):1568-1572, 2006.

Poly Allyl Amine (PAA)

CoPolymer of secondary amine and sulfur dioxide (PAS-92)

CoPolymer of primary amine and secondary amine (PAA-D41-HCl)

Sodium PyroPhosphate

Sodium TriPolyPhosphate

Sodium TriMetaPhosphate

Sodium HexaMetaPhosphate

Colors are NOT representations of the actual color

POLYELECTROLYTE DENTAL ADHESIVES FOR WHITENING TEETH AND TEETH COMPONENTS

CROSS-REFERENCE TO RELATED APPLICATIONS

This application is a continuation of U.S. application Ser. No. 15/473,355, filed Mar. 29, 2017 (now U.S. Pat. No. 9,937,120), which claims the benefit of U.S. Provisional Application Ser. No. 62/314,798, filed Mar. 29, 2016. The disclosure of the prior applications are considered part of (and are incorporated by reference in) the disclosure of this application.

BACKGROUND

1. Technical Field

This document relates to methods and materials involved in providing a tooth, tooth component, or inorganic dental material (e.g., a human tooth, a human tooth component, or an inorganic dental material within a human's mouth) with a white appearance. For example, the document relates to methods and materials for contacting a tooth, tooth component, or inorganic dental material with a whitening adhesive (e.g., a polyelectrolyte whitening adhesive) containing a conjugate of at least a polyamine, a polyphosphate, and one or more whitening agents (e.g., titanium dioxide and/or hydroxyapatite) to provide teeth with a whiter appearance.

2. Background Information

White teeth are considered cosmetically desirable. However, teeth can become discolored in the absence of intervention. The tooth structure that is generally responsible for presenting a stained appearance is the enamel layer. Several factors can contribute to enamel discoloration. For example, the formation of plaque and tartar matrices on the tooth surface can entrap stains, thereby leading to enamel discoloration.

Over-the-counter tooth whitening preparations have been developed to address the cosmetic preference of many to restore luster to tooth enamel discolored by surface entrapped materials. While all dentifrices and mouthwashes contain some cleaning and polishing agents, some enamel deposits become intractable to being fully removed by these agents under normal use conditions. Smokers often develop discolored enamel because the tars and particulates in cigarette smoke collect on the teeth. In some case, foods and drinks (e.g., tea) and/or antibiotics (e.g., tetracycline) can stain or discolor tooth enamel.

SUMMARY

This document provides methods and materials for contacting a tooth, tooth component, or inorganic dental material (e.g., a human tooth, a human tooth component, or an inorganic dental material within a human's mouth) with a whitening adhesive (e.g., a polyelectrolyte whitening adhesive) containing a conjugate of at least a polyamine, a polyphosphate, and one or more whitening agents (e.g., titanium dioxide ($TiO_2$) and/or hydroxyapatite (HA)) to provide the tooth, tooth component, or inorganic dental material with a whiter appearance. For example, a whitening adhesive containing a conjugate of at least a polyamine, a polyphosphate, and a whitening agent (e.g., $TiO_2$ and/or HA) can be used to provide teeth with a whiter appearance. In some cases, a whitening adhesive provided herein can be applied to a surface of a tooth, tooth component, or inorganic dental material. In some cases, a polyamine, a polyphosphate, and one or more whitening agents can be applied to a tooth, tooth component, or inorganic dental material, and a whitening adhesive can be formed on a surface of the tooth, tooth component, or inorganic dental material. The methods and materials provided herein can allow a person to have white appearing teeth even though the teeth may be stained. In some cases, white appearing teeth can be obtained using the methods and materials provided herein without harsh bleaching or de-staining techniques.

In general, one aspect of this document features a whitening adhesive. The whitening adhesive contains, or consists essentially of, a conjugate of a polyamine, a polyphosphate, and a whitening agent. The whitening agent has the ability to interact with or bind to a tooth, a tooth component, or an inorganic dental material. The whitening agent of the whitening adhesive provides teeth with a white appearance when the whitening adhesive is adhered to a tooth, a tooth component, or an inorganic dental material. The polyamine can be polyallylamine, PAS-92, PAA-D41, polylysine, or polyethyleneimine. The polyphosphate can be sodium hexametaphosphate, sodium trimetaphosphate, sodium tripolyphosphate, or sodium pyrophosphate. The whitening adhesive can have a w/w ratio of polyamine to polyphosphate of about 1:1 to about 1:20 (e.g., about 1:6.7). The whitening agent can include at least one of $TiO_2$, HA, silicon dioxide, zinc oxide (ZnO), bioactive glass, and blue fluorescent protein. The whitening agent can be $TiO_2$, where the $TiO_2$ comprises from about 0.05 wt % to about 2 wt % of the whitening adhesive. The whitening agent can be ZnO, where the ZnO comprises from about 0.5 wt % to about 10 wt % of the whitening adhesive. The whitening agent also can include HA, where the HA comprises from about 1 wt % to about 20 wt % of the whitening adhesive. The whitening agent also can include blue fluorescent protein.

In another aspect, this document features a method for altering an appearance of teeth. The method can include, or consist essentially or, applying to teeth a polyamine, a polyphosphate, and a whitening agent to form a whitening adhesive on a surface of said teeth, such that the whitening agent of the whitening adhesive can alter said appearance of the teeth. The teeth can be human teeth. The method can include altering the appearance of the teeth such that the teeth appear whiter. The polyamine can be polyallylamine, PAS-92, PAA-D41, polylysine, or polyethyleneimine. The polyphosphate can be sodium hexametaphosphate, sodium trimetaphosphate, sodium tripolyphosphate, or sodium pyrophosphate. The whitening adhesive can have a w/w ratio of polyamine to polyphosphate of about 1:1 to about 1:20 (e.g., about 1:6.7). The whitening agent can include at least one of $TiO_2$, HA, silicon dioxide, ZnO, bioactive glass, and blue fluorescent protein. The whitening agent can be $TiO_2$, where the $TiO_2$ comprises from about 0.05 wt % to about 2 wt % of the whitening adhesive. The whitening agent can be ZnO, where the ZnO comprises from about 0.5 wt % to about 10 wt % of the whitening adhesive. The whitening agent also can include HA, and where the HA comprises from about 1 wt % to about 20 wt % of the whitening adhesive. The whitening agent also can include blue fluorescent protein. Fluorescence emitted from the blue fluorescent protein can alter the appearance of said teeth such that said teeth appear whiter. The applying step can occur in the presence of saliva.

In another aspect, this document features a toothpaste. The toothpaste can include a polyamine, a polyphosphate, and a whitening agent, such that the polyamine, the polyphosphate, and the whitening agent form a whitening adhesive on a surface of a tooth, a tooth component, or an inorganic dental material when said toothpaste is applied to the tooth, the tooth component, or the inorganic dental material. The whitening agent of the whitening adhesive can alter the appearance of said tooth, said tooth component, or said inorganic dental material. The whitening adhesive can include from about 1 wt % to about 10 wt % polyamine.

In another aspect, this document features a mouth rinse. The mouth rinse can include a polyamine, a polyphosphate, and a whitening agent, such that the polyamine, the polyphosphate, and the whitening agent form a whitening adhesive on a surface of a tooth, a tooth component, or an inorganic dental material when the mouth rinse is applied to the tooth, the tooth component, or the inorganic dental material. The whitening agent of the whitening adhesive can alter the appearance of said tooth, said tooth component, or said inorganic dental material. The whitening adhesive can include from about 0.1 wt % to about 1 wt % polyamine.

In another aspect, this document features a kit. The kit can include a first composition comprising a polyamine and a whitening agent and a second composition comprising a polyphosphate. Contacting the first composition with the second composition can form a whitening adhesive including, or consisting essentially of, a conjugate of the polyphosphate, the polyamine, and the whitening agent. The whitening agent of the whitening adhesive can alter an appearance of a tooth, a tooth component, or an inorganic dental material when the whitening adhesive is applied to the tooth, the tooth component, or the inorganic dental material.

In another aspect, this document features a method for altering an appearance of a tooth, tooth component, or inorganic dental material. The method can include applying a polyamine and a whitening agent to the tooth, tooth component, or inorganic dental material, and applying a polyphosphate to the tooth, tooth component, or inorganic dental material such that the polyphosphate, the polyamine, and the whitening agent form a whitening adhesive on a surface of the tooth, tooth component, or inorganic dental material when applied to the tooth, tooth component, or inorganic dental material. The whitening agent of the whitening adhesive can alter the appearance of the tooth, tooth component, or inorganic dental material.

In another aspect, this document features a method for altering an appearance of a tooth, tooth component, or inorganic dental material. The method can include applying to teeth a conjugate including, or consisting essentially of, at least a polyamine, a polyphosphate, and a whitening agent, to form a coating on a surface of the teeth. The coating can alter the appearance of the teeth. The teeth can be human teeth. The method can alter the appearance of the teeth such that the teeth appear whiter. The polyamine can be polyallylamine, PAS-92, PAA-D41, polylysine, or polyethyleneimine. The polyphosphate can be sodium hexametaphosphate, sodium trimetaphosphate, sodium tripolyphosphate, or sodium pyrophosphate. The coating can include a w/w ratio of polyamine to polyphosphate of about 1:1 to about 1:20 (e.g., about 1:6.7). The whitening agent can include at least one of $TiO_2$, HA, silicon dioxide, ZnO, and blue fluorescent protein. The whitening agent can be $TiO_2$, where the $TiO_2$ comprises from about 0.05 wt % to about 2 wt % of the whitening adhesive. The whitening agent can be ZnO, where the ZnO comprises from about 0.5 wt % to about 10 wt % of the whitening adhesive. The whitening agent also can include HA, where the HA comprises from about 1 wt % to about 20 wt % of the whitening adhesive. The whitening agent also can include blue fluorescent protein. Fluorescence emitted from the blue fluorescent protein can alter the appearance of the teeth such that the teeth appear whiter. The applying step can occur in the presence of saliva.

In another aspect, this document features a whitening adhesive comprising, or consisting essentially of, a conjugate of a polyamine, a polyphosphate, and a whitening agent and having the ability to interact with or bind to a tooth, a tooth component, or an inorganic dental material. The whitening agent of the whitening adhesive provides teeth with a white appearance when the whitening adhesive is adhered to the tooth, the tooth component, or the inorganic dental material, wherein the polyamine comprises from about 5 wt % to about 15 wt % of the whitening adhesive, wherein the polyphosphate comprises from about 25 wt % to about 35 wt % of the whitening adhesive, and wherein the whitening agent comprises from about 10 wt % to about 20 wt % of the whitening adhesive. The polyamine can be selected from the group consisting of polyallylamine, PAS-92, PAA-D41, polylysine, and polyethyleneimine. The polyphosphate can be selected from the group consisting of sodium hexametaphosphate, sodium trimetaphosphate, sodium tripolyphosphate, and sodium pyrophosphate. The whitening agent can comprise at least one of titanium dioxide, hydroxyapatite, silicon dioxide, zinc oxide, and blue fluorescent protein. The polyamine can be PAA-D41, the polyphosphate can be sodium trimetaphosphate, and the whitening agent can be zinc oxide. The polyamine can be polyallylamine, the polyphosphate can be sodium trimetaphosphate, and the whitening agent can be zinc oxide.

In another aspect, this document features a method for altering an appearance of teeth. The method comprises, or consists essentially of, applying to teeth a whitening adhesive comprising, or consisting essentially of, a conjugate of a polyamine, a polyphosphate, and a whitening agent and having the ability to interact with or bind to a tooth, a tooth component, or an inorganic dental material. The whitening agent of the whitening adhesive provides teeth with a white appearance when the whitening adhesive is adhered to the tooth, the tooth component, or the inorganic dental material, wherein the polyamine comprises from about 5 wt % to about 15 wt % of the whitening adhesive, wherein the polyphosphate comprises from about 25 wt % to about 35 wt % of the whitening adhesive, and wherein the whitening agent comprises from about 10 wt % to about 20 wt % of the whitening adhesive. The polyamine can be selected from the group consisting of polyallylamine, PAS-92, PAA-D41, polylysine, and polyethyleneimine. The polyphosphate can be selected from the group consisting of sodium hexametaphosphate, sodium trimetaphosphate, sodium tripolyphosphate, and sodium pyrophosphate. The whitening agent can comprise at least one of titanium dioxide, hydroxyapatite, silicon dioxide, zinc oxide, and blue fluorescent protein. The polyamine can be PAA-D41, the polyphosphate can be sodium trimetaphosphate, and the whitening agent can be zinc oxide. The polyamine can be polyallylamine, the polyphosphate can be sodium trimetaphosphate, and the whitening agent can be zinc oxide.

Unless otherwise defined, all technical and scientific terms used herein have the same meaning as commonly understood by one of ordinary skill in the art to which this disclosure pertains. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3A shows preparation of a dilute whitening adhesive in large volumes. FIG. 3B shows preparation of a concentrated whitening adhesive in small volumes.

FIG. 9A contains photographs showing the appearance of whiter teeth following application of an exemplary whitening adhesive containing a conjugate of PAA, various polyphosphates (STP, SHMP, PP, and TPP), and $TiO_2$. FIG. 9B contains photographs showing the appearance of whiter teeth following application of an exemplary whitening adhesive containing a conjugate of PAS-92, various polyphosphates (STP, SHMP, PP, and TPP), and $TiO_2$.

DETAILED DESCRIPTION

Figure 1:
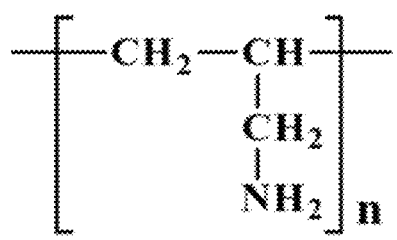
FIG. 1 shows examples of polyamines: polyallylamine (PAA), a co-polymer of secondary amine and sulfur dioxide (PAS-92), and a copolymer of primary amine and secondary amine (PAA-D41-HCl).
Figure 1:
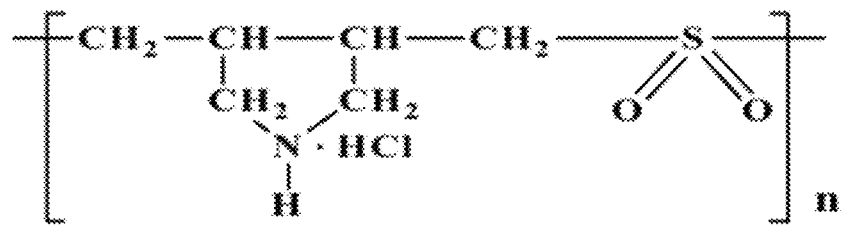
Figure 1:
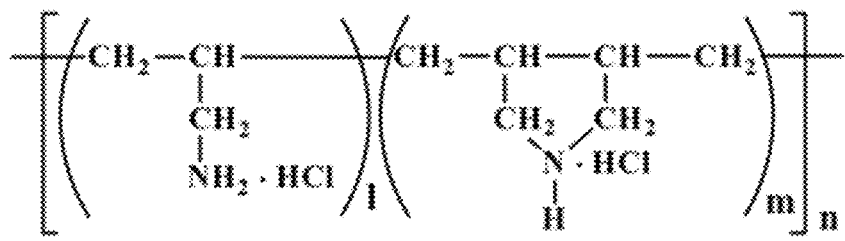
Figure 2:
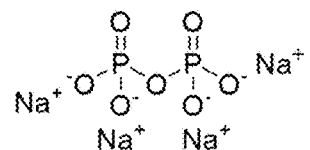
FIG. 2 shows examples of polyphosphates: sodium pyrophosphate (PP), sodium tripolyphosphate (TPP), sodium trimetaphosphate (STP), and sodium hexametaphosphate (SHMP).
Figure 2:
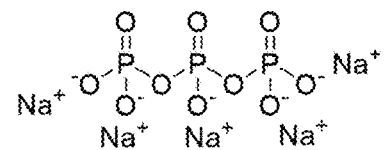
Figure 2:
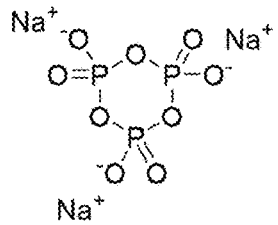
Figure 2:
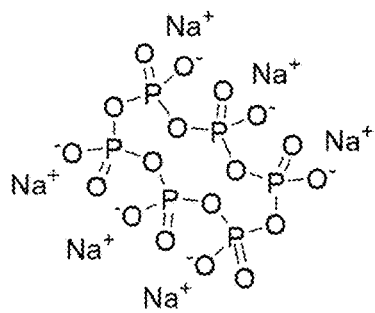

This document provides methods and materials for using a whitening adhesive (e.g., a polyelectrolyte whitening adhesive) containing a conjugate of at least a polyamine, a polyphosphate, and one or more whitening agents (e.g., $TiO_2$, ZnO, and/or HA) to adhere to a tooth, a tooth component, or an inorganic dental material (e.g., a human tooth, a human tooth component, or an inorganic dental material within a human's mouth). For example, this document provides methods and materials for adhering or attaching a whitening agent to teeth as a coating to provide a whiter appearance. In some cases, this document provides methods and materials for contacting teeth with a whitening adhesive containing a conjugate of at least a polyamine, a polyphosphate, and one or more whitening agents to provide the teeth with a coating that provides a whiter appearance that can be maintained after brushing.

A whitening adhesive containing a conjugate of at least a polyamine, a polyphosphate, and one or more whitening agents (e.g., $TiO_2$, ZnO, and/or HA) can be a polyelectrolyte adhesive and can have the ability to interact with or bind to a tooth, a tooth component (e.g., enamel, hydroxyapatite, acquired dental pellicle, cementum, crown, cervix, cementoenamel junction, or apex), or inorganic dental materials (e.g., crowns, caps, braces, or fillings) using weak or strong ionic or covalent interactions to the surface of the tooth, tooth component, or inorganic dental material, thus attaching or adhering a whitening agent to the tooth, tooth component, or inorganic dental material. A whitening adhesive (e.g., a polyelectrolyte whitening adhesive) can adhere to organic or inorganic materials on the surface of a tooth, tooth component, or inorganic dental material. A tooth, tooth component, or inorganic dental material can be from a mammal (e.g., a human, dog, cat, cow, or horse).

A whitening adhesive (e.g., a polyelectrolyte whitening adhesive) can be formed by contacting a polycation, a polyanion, and one or more whitening agents (e.g., $TiO_2$, ZnO, and/or HA). For example, a whitening adhesive can be formed by contacting a polyamine, a polyphosphate, and one or more whitening agents. When forming a whitening adhesive described herein, the polyamine, the polyphosphate, and the one or more whitening agents can be provided separately, together, or in any combination. In cases where a polyamine, a polyphosphate, and one or more whitening agents are provided separately, they can be provided simultaneously or serially. A polyamine, a polyphosphate, and one or more whitening agents provided serially can be provided in any order. In some cases, a whitening adhesive provided herein can be formed by contacting a first composition containing a polyphosphate (e.g., STP) to a second composition containing a polyamine (e.g., PAA) and a whitening agent (e.g., $TiO_2$). In some cases, a whitening adhesive provided herein can be formed by contacting a first composition containing a polyphosphate (e.g., STP) and one or more whitening agents to a second composition containing a polyamine (e.g., PAA). When forming a whitening adhesive described herein, the polyamine, the polyphosphate, and the one or more whitening agents can be provided in any form (e.g., a solution, powder, gel, or suspension). In some cases, a whitening adhesive provided herein can be formed by contacting a powder form of a polyphosphate (e.g., STP) to a solution containing a polyamine (e.g., PAA) and one or more whitening agents (e.g., $TiO_2$, ZnO, and/or HA).

Any appropriate polyamine can be used to form a whitening adhesive described herein. A polyamine can be a polymer containing repeating units of primary amines, secondary amines, amines mixed with other repeat units (e.g., such as sulfur dioxide), or combinations thereof. Examples of a polyamines that can be used to form a whitening adhesive described herein include, without limitation, PAA, copolymers of a primary and secondary amine (e.g. PAA-D41-HCl), copolymers of secondary amine and sulfur dioxide (e.g., PAS-92), PAA hydrochloride, polydiallylamine (DAA), polyampholite, chitosan, polylysine, polyvinyl amine, polyethyleneimine (PEI), heparin, and EUDRAGIT® E 100. A polyamine polymer described herein can be a hydrochloride salt form or a free base form. Additional examples of polyamines that can be used to form a whitening adhesive described herein include, without limitation, those commercially available from Nittobo Medical Co., LTD (see, e.g., the PAS series, the PAA series, and the polyampholite series). A polyamine used to form a whitening adhesive described herein can be a homopolymer, copolymer, or a combination thereof. In some cases, a polyamine used as described herein can have a molecular weight of less than about 200,000 (e.g., less than about 100,000; less than about 50,000; less than about 30,000; less than about 15,000; or less than about 10,000). For example, a polyamine used as described herein can have a molecular weight of about 5,000 to about 20,000. In some cases, a polyamine used as described herein can have a pH of about 6 to about 10 (e.g., about 6.5 to about 9, about 7 to about 9.5, or about 8 to about 9). A polyamine can be pH adjusted to have a pH of about 6 to about 10.

A whitening adhesive containing a conjugate of at least a polyamine, a polyphosphate, and one or more whitening agents described herein can include from about 0.1 weight percent to about 10 weight percent of the polyamine (e.g., PAA, PAA-D41-HCl, PAS-92, PEI, or polylysine). In some cases, a dilute whitening adhesive can be used, for example, as a mouth rinse, and can include about 0.1 wt % to about 1 wt % (e.g., from about 0.2 wt % to about 0.9 wt %, from about 0.3 wt % to about 0.8 wt %, from about 0.4 wt % to about 0.7 wt %, or from about 0.5 wt % to about 0.6 wt %) polyamine. In some cases, a concentrated whitening adhesive can be used, for example, as a toothpaste or gel, and can include about 1 wt % to about 10 wt % (e.g., from about 2 wt % to about 9 wt %, from about 3 wt % to about 8 wt %, from about 4 wt % to about 7 wt %, from about or from about 5 wt % to about 6 wt %) polyamine.

Any appropriate polyphosphate can be used to form a whitening adhesive described herein. A polyphosphate can be a cyclic polyphosphate, a linear polyphosphate, a potassium salt of a polyphosphate, or a sodium phosphate salt of a polyphosphate. A polyphosphate can be a polymer having any phosphate-containing compound or salt thereof. Examples of polyphosphates that can be used as described herein include, without limitation, hexametaphosphate (e.g., SHMP), trimetaphosphate (e.g., STP), tripolyphosphate (e.g., TPP), pyrophosphate (e.g., PP). Optionally, other poly-acids can also be introduced such as alginates (e.g., alginic acid), crosslinked with $CaCl_2$), carrageenan, poly-lactic-co-glycolic acid (PLGA), polyacrylic acid, polystyrenesulfate, polyvinyl sulfate, polyglutamic acid, and/or polyaspartic acid. A polyphosphate used to form a whitening adhesive described herein can be a homopolymer, copolymer, or a combination thereof. In some cases, a polyphosphate used as described herein can have a molecular weight greater less than about 50,000 (e.g., less than about 20,000; less than about 5,000; less than about 3,000; less than about 2,000; or less than about 1,000). In some cases, a polyphosphate can aid in enamel remineralization.

A whitening adhesive containing a conjugate of at least a polyamine, a polyphosphate, and one or more whitening agents described herein can include from about 0.05 wt % to about 25 wt % of polyphosphate (e.g., STP, SHMP, TPP, or PP). In some cases, a dilute whitening adhesive can be used, for example, as a mouth rinse, and can include about 0.05 wt % to about 1 wt % (e.g., from about 0.1 wt % to about 0.9 wt %, from about 0.15 wt % to about 0.8 wt %, from about 0.2 wt % to about 0.7 wt %, or from about 0.25 wt % to about 0.6 wt %) polyphosphate. In some cases, a concentrated whitening adhesive can be used, for example, as a toothpaste or gel, and can include about 1 wt % to about 25 wt % (e.g., from about 2 wt % to about 20 wt %, from about 3 wt % to about 15 wt %, from about 4 wt % to about 10 wt %, or from about 5 wt % to about 8 wt %) polyphosphate. In some cases, the wt % of the polyphosphate can be comparable to the wt % of the polyamine. In some cases, the wt % of the polyphosphate can be higher (e.g., 2 times (2×) higher, 3× higher, 5× higher, 7× higher, 10× higher, or 20× higher) than the wt % of the polyamine.

In some cases, a whitening adhesive containing a conjugate of at least a polyamine, a polyphosphate, and one or more whitening agents described herein can include a w/w ratio of polyamine (e.g., PAA, PAA-D41-HCl, PAS-92, PEI, and/or polylysine) to polyphosphate (e.g., STP, SHMP, TPP, and/or PP) of about 5:1 to about 1:20 (e.g., about 2:1 to about 1:18, about 1:1 to about 1:15, about 1:1 to about 1:12, about 1:1 to about 1:10, about 1:2 to about 1:9, about 1:3 to about 1:8, or about 1:5 to about 1:8). For example, a whitening adhesive described herein can include a w/w ratio of polyamine to polyphosphate of about 1:6.7. In some cases, a whitening adhesive containing a conjugate of at least a polyamine, a polyphosphate, and one or more whitening agents described herein can include a w/w ratio of polyamine (e.g., PAA, PAA-D41-HCl, PAS-92, PEI, and/or polylysine) to polyphosphate (e.g., STP, SHMP, TPP, and/or PP) of about 10:1 to about 1:10.

Any appropriate method can be used to make a whitening adhesive containing a conjugate of at least a polyamine, a polyphosphate, and one or more whitening agents described herein, and having the ability to interact with and/or bind to tooth, tooth component, or inorganic dental material. In some cases, a polyamine and/or a polyphosphate can be obtained from a commercial source or can be synthesized from the polymerization of a desired monomer or combination of different monomers. In some cases, standard polymer synthesis techniques (e.g., addition polymerization, sol-gel synthesis, phase separation, template-assisted synthesis, step growth polymerization, or co-polymerization using chemical or photochemical radical synthesis) can be used to produce polyamines and/or polyphosphates.

Any appropriate whitening agent can be used to form a whitening adhesive described herein. Examples of whitening agents that can be used in a whitening adhesive described herein include, without limitation, particles composed of $TiO_2$, ZnO, HA, silicon dioxide ($SiO_2$), bioactive glass, zirconium silicate, and/or calcium phosphate. See, e.g., Schilling et al., *Photochem. Photobiol. Sci.,* 9:495-509 (2010); and U.S. Pat. No. 6,004,567. Particulate whitening agents can range in size from about 5 nanometer (nm) to about 1000 nm (1 μm) in size (e.g., from about 10 nm to about 900 nm, from about 25 nm to about 750 nm, from about 50 nm to about 500 nm, from about 75 nm to about 450 nm, from about 100 nm to about 400 nm, from about 125 nm to about 350 nm, or from about 150 nm to about 300 nm).

In some cases, BFP can be used as a whitening agent to make a whitening adhesive provided herein. See, e.g., U.S. Pat. No. 8,568,698; and U.S. Pat. No. 8,784,783. For example, a polypeptide that emits blue fluorescence can be combined with a polyamine and a polyphosphate to form a whitening adhesive described herein for coating teeth to provide a whiter appearance. A BFP can have an emission wavelength from about 400 nm to about 500 nm (e.g., from about 410 nm to about 500 nm, from about 420 nm to about 500 nm, from about 430 nm to about 500 nm, from about 440 nm to about 500 nm, from about 440 nm to about 490 nm, from about 440 nm to about 480 nm, from about 440 nm to about 470 nm, from about 440 nm to about 460 nm, from about 450 nm to about 490 nm, or from about 460 nm to about 480 nm). In some cases, a fluorescent polypeptide that emits fluorescence at an emission wavelength of from about 490 nm to about 600 nm (e.g., from about 430 nm to about 450 nm, from about 440 nm to about 450 nm, from about 420 nm to about 440 nm, or from about 485 nm to about 505 nm) can be used as a whitening agent to make a composition provided herein, and can be applied to teeth as described herein.

In some cases, a whitening adhesive containing a conjugate of at least a polyamine, a polyphosphate, and one or more whitening agents described herein can include two or more whitening agents (e.g., two whitening agents, three whitening agents, four whitening agents, or five whitening agents). For example, a whitening adhesive can include $TiO_2$ and HA; $TiO_2$ and BFP; HA and BFP; $TiO_2$, HA and BFP; $TiO_2$ and ZnO; $TiO_2$ and $SiO_2$; HA and $SiO_2$; or $TiO_2$, HA, $SiO_2$, ZnO and BFP. A whitening agent can be covalently or non-covalently attached to any component of a whitening adhesive such as a polyamine and/or a polyphosphate.

A whitening adhesive containing a conjugate of at least a polyamine, a polyphosphate, and one or more whitening agents described herein can include from about 0.05 weight percent to about 20 weight percent whitening agent. For example, a whitening adhesive described herein can include from about 0.05 weight percent to about 2 weight percent (e.g., from about 0.07 wt % to about 1.9 wt %, from about 0.09 wt % to about 1.8 wt %, or from about 1 wt % to about 1.5 wt %) $TiO_2$. For example, a whitening adhesive described herein can include from about 0.5 wt % to about 10 wt % (e.g., from about 0.7 wt % to about 9 wt %, from about 0.9 wt % to about 8 wt %, or from about 1 wt % to about 7 wt %) ZnO. For example, a whitening adhesive described herein can include from about 1 wt % to about 20 wt % (e.g., from about 2 wt % to about 19 wt %, from about 3 wt % to about 18 wt %, from about 4 wt % to about 17 wt %, or from about 5 wt % to about 15 wt %) HA.

In some cases, a whitening adhesive containing a conjugate of one or more polyamines, one or more polyphosphates, and one or more whitening agents described herein can include from about 0.1 wt % to about 15 wt % (e.g., from about 3.5 wt % to about 15 wt %, from about 5 wt % to about 15 wt %, from about 7 wt % to about 15 wt %, from about 3.5 wt % to about 11 wt %, from about 3.5 wt % to about 10 wt %, from about 5 wt % to about 12 wt %, from about 6 wt % to about 8 wt %, or from about 9 wt % to about 11 wt %) of polyamine(s), from about 0.05 wt % to about 60 wt % (e.g., from about 1 wt % to about 60 wt %, from about 5 wt % to about 60 wt %, from about 10 wt % to about 60 wt %, from about 20 wt % to about 60 wt %, from about 25 wt % to about 60 wt %, from about 5 wt % to about 50 wt %, from about 5 wt % to about 40 wt %, from about 20 wt % to about 40 wt %, from about 25 wt % to about 35 wt %, from about 7.5 wt % to about 15 wt %, or from about 9 wt % to about 12 wt %) of polyphosphate(s), and from about 0.05 wt % to about 45 wt % (e.g., from about 5 wt % to about 45 wt %, from about 5 wt % to about 40 wt %, from about 5 wt % to about 35 wt %, from about 5 wt % to about 30 wt %, from about 10 wt % to about 45 wt %, from about 15 wt % to about 45 wt %, from about 20 wt % to about 45 wt %, from about 10 wt % to about 20 wt %, from about 12 wt % to about 17 wt %, from about 20 wt % to about 40 wt %, from about 25 wt % to about 35 wt %, from about 28 wt % to about 33 wt %, from about 30 wt % to about 45 wt %, or from about 35 wt % to about 40 wt %) of whitening agent(s). In some cases, a whitening adhesive containing a conjugate of one or more polyamines, one or more polyphosphates, and one or more whitening agents described herein can include from about 5 Wt % to about 15 wt % of a polyamine such as PAA-D41, from about 25 wt % to about 35 wt % of a polyphosphate such as STP, and from about 10 wt % to about 20 wt % of a whitening agent such as ZnO. In some cases, a whitening adhesive containing a conjugate of one or more polyamines, one or more polyphosphates, and one or more whitening agents described herein can include from about 5 wt % to about 15 wt % of a polyamine such as PAA, from about 25 wt % to about 35 wt % of a polyphosphate such as STP, from about 10 wt % to about 20 wt % of a whitening agent such as ZnO, and from about 0.1 wt % to about 5 wt % of a whitening agent such as $TiO_2$. In some cases, a whitening adhesive containing a conjugate of one or more polyamines, one or more polyphosphates, and one or more whitening agents described herein can include from about 5 wt % to about 15 wt % of a polyamine such as PAA-D41, from about 25 wt % to about 35 wt % of a polyphosphate such as TPP, and from about 10 wt % to about 20 wt % of a whitening agent such as ZnO. In some cases, a whitening adhesive containing a conjugate of one or more polyamines, one or more polyphosphates, and one or more whitening agents described herein can include from about 5 wt % to about 15 wt % of a polyamine such as PAA-D41, from about 25 wt % to about 35 wt % of a polyphosphate such as TPP, and from about 1 wt % to about 10 wt % of a whitening agent such as ZnO. In some cases, a whitening adhesive containing a conjugate of one or more polyamines, one or more polyphosphates, and one or more whitening agents described herein can include from about 5 wt % to about 15 wt % of a polyamine such as PAA, from about 25 wt % to about 35 wt % of a polyphosphate such as STP, from about 20 wt % to about 30 wt % of a whitening agent such as ZnO, and from about 0.1 wt % to about 5 wt % of a whitening agent such as $TiO_2$. In some cases, a whitening adhesive containing a conjugate of one or more polyamines, one or more polyphosphates, and one or more whitening agents described herein can include from about 1 wt % to about 10 wt % of a polyamine such as PAA, from about 5 wt % to about 15 wt % of a polyphosphate such as STP, from about 5 wt % to about 20 wt % of a whitening agent such as ZnO, and optionally from about 0.1 wt % to about 5 wt % of a whitening agent such as $TiO_2$. In some cases, a whitening adhesive containing a conjugate of one or more polyamines, one or more polyphosphates, and one or more whitening agents described herein can include from about 5 wt % to about 15 wt % of a polyamine such as PAA, from about 25 wt % to about 35 wt % of a polyphosphate such as STP, and from about 10 wt % to about 20 wt % of a whitening agent such as ZnO.

A whitening adhesive containing a conjugate of at least a polyamine, a polyphosphate, and one or more whitening agents described herein also can contain one or more other molecules. For example, a whitening adhesive also can be combined with a therapeutic agent (e.g. fluoride and/or antibacterial compounds), remineralization particles (e.g., HA, fluoride, calcium, magnesium, phosphate, iron, and/or tin ions, and any salt forms thereof), astringent salts, odor neutralizers, anti-gingivitis agents, anti-plaque agents, anti-tartar agents, or any combination thereof.

This document also provides methods for applying a whitening adhesive containing a conjugate of at least a polyamine, a polyphosphate, and one or more whitening agents described herein. In some cases, a whitening adhesive can be formed and then applied directly to a tooth, tooth component, or inorganic dental material in a single step. In some cases, a polyamine, a polyphosphate, and one or more whitening agents can be applied to a tooth, tooth component, or inorganic dental material in separate steps and a whitening adhesive can be formed on the tooth, tooth component, or inorganic dental material. In cases where a polyamine, a polyphosphate, and one or more whitening agents are applied separately, the application can be simultaneous or non-simultaneous. For example, a polyamine, a polyphosphate, and one or more whitening agents can be applied to a tooth, tooth component, or inorganic dental material simultaneously using a multi-channel delivery applicator (e.g., a dual channel delivery applicator). For example, a polyamine, a polyphosphate, and one or more whitening agents can be applied non-simultaneously to a tooth, tooth component, or inorganic dental material using a first composition (e.g., containing a polyphosphate) which can be applied to the tooth, tooth component, or inorganic dental material first and a second composition (e.g., containing a polyamine and one or more whitening agents) which can be applied to the tooth, tooth component, or inorganic dental material immediately after.

In some cases, a whitening adhesive containing a conjugate of at least a polyamine, a polyphosphate, and one or more whitening agents described herein can be applied under conditions that allow a whitening agent to adhere directly or indirectly to a tooth, tooth component, or inorganic dental material to alter the appearance (e.g., color or smoothness) of the tooth, tooth component, or inorganic dental material. For example, an effective amount of a whitening adhesive provided herein can be delivered to a tooth, tooth component, or inorganic dental material such that the appearance of the tooth, tooth component, or inorganic dental material is altered (e.g., the appearance of the tooth, tooth component, or inorganic dental material becomes whiter).

A whitening adhesive containing a conjugate of at least a polyamine, a polyphosphate, and one or more whitening agents provided herein can be applied to a tooth, tooth component, or inorganic dental material under dry or wet conditions. In some cases, a whitening adhesive can be applied under typical conditions found in the mouth (e.g., the presence of saliva). For example, a whitening adhesive can be applied to a tooth, tooth component, or inorganic dental material in the presence of saliva to alter the appearance of the tooth, tooth component, or inorganic dental material.

Any appropriate formulation can be used to deliver a whitening adhesive containing a conjugate of at least a polyamine, a polyphosphate, and one or more whitening agents provided herein to a tooth, tooth component, or inorganic dental material. For example, a whitening adhesive provided herein can be incorporated into a toothpaste, a mouth wash, a mouth rinse, an ingestable substance such as a drink or a food product, gum (e.g., chewing gum), gels (an application gel), powders, or creams. For example, a whitening adhesive provided herein can be delivered on a film strip (e.g., a wax or plastic strip, such as a polyethylene strip) or applied directly to a tooth, tooth component, or inorganic dental material and covered with a film strip. For example, a whitening adhesive provided herein can be delivered in a dental tray or a mouth dam fit to a mammal's (e.g., a human's) tooth structure. In some cases, a formulation including a whitening adhesive provided herein can include one or more pharmaceutical excipients. For example, a toothpaste containing a whitening adhesive described herein can include one or more thickeners (e.g., cellulose derivatives, polyvinylpyrollidones, mineral colloids, or polyethylene glycol (PEG)), buffers, surfactants, fluorides, flavorings (e.g., peppermint, spearmint, wintergreen, or bubble gum), sweeteners (e.g., sucralose or xylitol), sugar alcohols (e.g., sorbitol, glycerol, or xylitol), sensitivity reducers (e.g., potassium nitrate), humectrants (e.g., glycerin), and/or anti-bacterial agents (e.g., Triclosan or zinc chloride) that do not interfere with altering the appearance (e.g., whitening) of a tooth, tooth component, or inorganic dental material.

An effective amount of a whitening adhesive containing a conjugate of at least a polyamine, a polyphosphate, and one or more whitening agents provided herein can be any appropriate amount that alters the appearance of a tooth, tooth component, or inorganic dental material without inducing significant toxicity. It will be appreciated that the amount can be higher for certain formulations, e.g., mouthwash.

In some cases, a whitening adhesive containing a conjugate of at least a polyamine, a polyphosphate, and one or more whitening agents provided herein can be applied to a tooth, tooth component, or inorganic dental material to give the tooth, tooth component, or inorganic dental material a whiter appearance, to prevent biofilms, and/or to repair enamel.

In some cases, a whitening adhesive containing a conjugate of at least a polyamine, a polyphosphate, and one or more whitening agents provided herein can be applied to a tooth, tooth component, or inorganic dental material for a period of time prior to washing, rinsing, or removal such that the appearance of the tooth, tooth component, or inorganic dental material is altered (e.g., the appearance of the tooth, tooth component, or inorganic dental material becomes whiter). For example, a toothpaste or other formulation configured to include a whitening adhesive containing a conjugate of at least a polyamine, a polyphosphate, and one or more whitening agents as described herein can be applied (e.g., applied directly or formed on) to a tooth, tooth component, or inorganic dental material and remain in contact with that tooth, tooth component, or inorganic dental material, without rinsing, for from about 30 seconds to about 60 minutes (e.g., from about 30 seconds to about 45 minutes, from about 30 seconds to about 30 minutes, from about 30 seconds to about 25 minutes, from about 1 minute to about 20 minutes, from about 2 minutes to about 15 minutes, from about 3 minutes to about 10 minutes, or from about 4 minutes to about 6 minutes). In some cases, such as with a mouth wash, mouth rinse, or application gel, a whitening adhesive can be allowed to be in contact with a tooth, tooth component, or inorganic dental material for a period of time for the composition to saturate the tooth, tooth component, or inorganic dental material.

In some cases, a tooth, tooth component, or inorganic dental material (e.g., a human's tooth) can be prepared prior to applying a whitening adhesive containing a conjugate of at least a polyamine, a polyphosphate, and one or more whitening agents provided herein. For example, a tooth, tooth component, or inorganic dental material can be washed, brushed, or polished (e.g., polished with pumice) prior to applying a whitening adhesive provided herein. In some cases, the surface of the tooth, tooth component, or inorganic dental material can be treated with one or more agents capable of exposing calcium phosphate binding sites. For example, a tooth, tooth component, or inorganic dental material to be treated with a whitening adhesive provided herein can be contacted with EDTA or phosphoric acid to expose calcium phosphate binding sites present on the tooth, tooth component, or inorganic dental material. In the case of phosphoric acid treatment, only tooth enamel can be exposed to the acid to prevent or reduce the risk of soft tissue damage.

In some cases, an assay can be performed to confirm that a whitening adhesive containing a conjugate of at least a polyamine, a polyphosphate, and one or more whitening agents provided herein or a component of a composition provided herein has binding affinity for a tooth, tooth component, or inorganic dental material. For example, a material to be tested can be incubated with a HA matrix, and the amount of material in solution after HA binding can be compared with the initial concentration to determine, by difference, the amount of bound material. See, e.g., Raj et al., *J. Biol. Chem.*, 267:5968-5976 (1992). In some cases, the HA bound material can be directly measured after dissolving the HA matrix with EDTA (Lamkin et al., *J. Dent. Res.*, 75:803-808 (1996)). In some cases, an assay can be performed with an HA matrix that was pre-incubated with human saliva to coat the HA with proteins as described elsewhere (Lamkin et al., *J. Dent. Res.*, 75:803-808 (1996)). In such cases, unbound saliva proteins can be removed by washing since their presence may interfere with the polyelectrolyte concentration determinations.

Any appropriate method can be used to assess the affinity of a whitening adhesive containing a conjugate of at least a polyamine, a polyphosphate, and one or more whitening agents provided herein for a tooth, tooth component, inorganic dental material, or an HA matrix. For example, bound and unbound whitening adhesive can be quantified, when a fluorescent polypeptide such as BFP is used, by measuring the fluorescence of the fluorescence emitting polypeptide of the composition. In some cases, a whitening adhesive provided herein can be assessed for the ability to bind in vitro to a human tooth or a human tooth component. The tooth or tooth component can be subjected to different degrees of cleaning, such as brushing or polishing with pumice. The tooth or tooth component can then be treated with human saliva to form the acquired dental pellicle and incubated with a whitening adhesive provided herein in the presence and absence of saliva. The binding to the tooth or tooth component can be determined by measuring the degree of whiteness.

Any appropriate method can be used to assess a whitening adhesive containing a conjugate of at least a polyamine, a polyphosphate, and one or more whitening agents provided herein for the ability to alter the appearance of a tooth, tooth component, or inorganic dental material. For example, visual inspection techniques can be used to determine whether or not a whitening adhesive provided herein can alter the appearance of a tooth, tooth component, or inorganic dental material. Such visual inspection techniques can include using shade guides for comparison as described elsewhere (Paravina et al., *J. Esthet. Restor. Dent.*, 19:276-283 (2007)). In some cases, the ability of a whitening adhesive provided herein to alter the appearance of a tooth, tooth component, or inorganic dental material (e.g., to make a tooth, tooth component, or inorganic dental material appear whiter) can be measured using reflectance spectrophotometry. In such cases, the tooth, tooth component, or inorganic dental material can be illuminated with a white light source and analyzed as to the amount of light absorbed at different wavelengths by reflectance spectrophotometry (colorimetry). These measurements can then be repeated with the UV light filtered from the light source. The difference in the reflectance values obtained with the inclusion and exclusion of UV light is the UV fluorescence spectrum of the tooth surface (see, e.g., Park et al., *Dental Materials*, 23:731-735 (2007)).

A whitening adhesive containing a conjugate of at least a polyamine, a polyphosphate, and one or more whitening agents (e.g., $TiO_2$ and/or ZnO) provided herein can lack dyes, which can potentially have toxic properties.

The invention will be further described in the following examples, which do not limit the scope of the invention described in the claims.

EXAMPLES

Figure 3A:
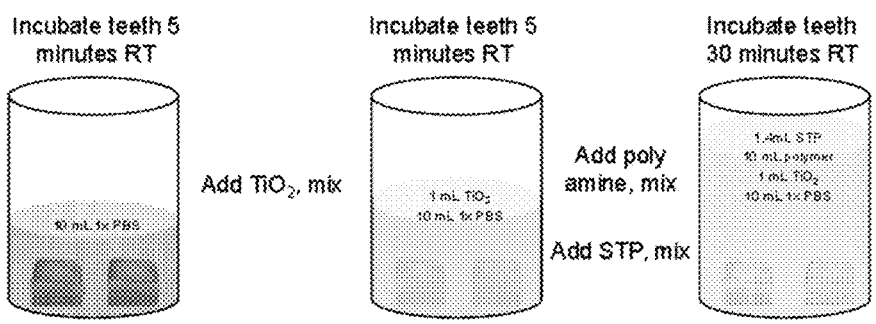
FIGS. 3A and 3B are schematic diagrams of exemplary procedures for the preparation of a whitening adhesive.

Example 1: Preparation of Polyelectrolyte Adhesive Whitening Solution or Gel To prepare a whitening adhesive, 1 wt % whitening agent (e.g., titanium dioxide and/or zinc oxide optionally containing hydroxyapatite, blue fluorescent protein, silicon dioxide, bioactive glass or others) was added to water and/or a thickening agent (e.g., polyvinylpyrrolidone, such as Kollidon K90F, or Cellulose Gum) containing the tooth specimens incubated for 5 minutes, followed by addition of 5 wt % polymer (e.g., PAA, PAS-92, or PAA-D41 adjusted to pH 7 to 9). A 5 wt % phosphate reagent (e.g., STP, SHMP, TPP, PP) was added, and the mixture was incubated for 30 minutes, followed by rinsing with water and brushing for 10 seconds with an electric toothbrush. A picture depicting the scheme of this preparation method is shown in FIG. 3A.

The compositions of the polyelectrolyte mixtures are shown in Table 1.

TABLE 1

| Reagent | Stock Conc. (%) | Amount Added (mL) | Final Conc. (Cf, Wt %) |
| --- | --- | --- | --- |
| water/Thickening agent | 1 | 10 | 0.446 |
| TiO2 | 1 | 1 | 0.045 |
| STP | 5.7 | 1.4 | 0.356 |
| Polymer | 2.5 | 10 | 1.116 |
| Total | | 22.4 | |

Figure 4:
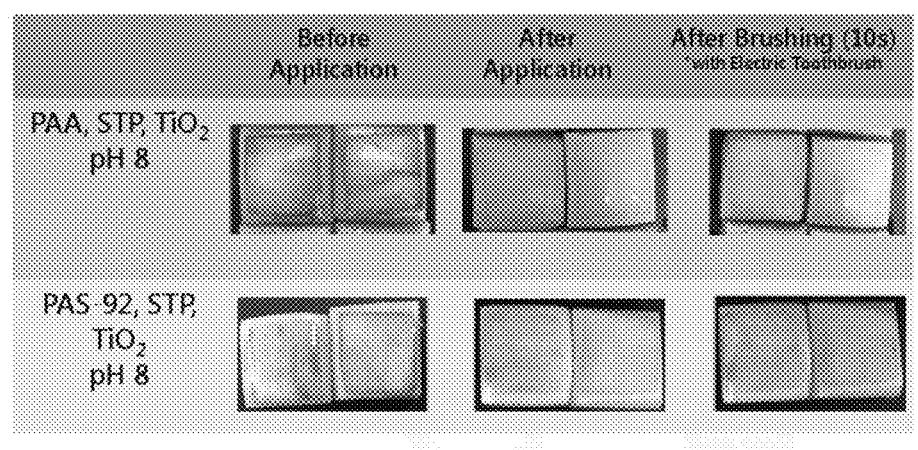
FIG. 4 contains photographs showing the appearance of whiter teeth following application of an exemplary whitening adhesive containing a conjugate of PAA, STP, and $TiO_2$ (top panel) or a conjugate of PAS-92, STP, and $TiO_2$ (bottom panel), as described in exemplary procedure FIG. 3A.

FIG. 4 contains photographs showing the appearance of whiter teeth following application of an exemplary whitening adhesive containing polyallylamine (PAA), sodium trimetaphosphate (STP), and titanium dioxide ($TiO_2$) (top panel) or an exemplary whitening adhesive containing PAS-92, STP, and $TiO_2$ (bottom panel).

Example 2: Polyelectrolyte Adhesive with a Whitening Agent on a Tooth Component Preparations of polyelectrolyte whitening adhesives containing either PAA, STP, and $TiO_2$; PAS-92, STP, and $TiO_2$; or PAA-D41, STP, and $TiO_2$ were prepared as described below.

To prepare a whitening adhesive, 1 wt % whitening agent (e.g., titanium dioxide and/or zinc oxide optionally containing hydroxyapatite, blue fluorescent protein, silicon dioxide, bioactive glass or others) was added to a solution of 14 wt % polymer (e.g., PAA, PAS-92, or PAA-D41 adjusted to a pH between 7 and 9), such that the whitening agent concentration was 0.2 wt % and polymer was 0.75 wt % in a tube labelled as "A". A 25 wt % phosphate reagent (e.g., STP, SHMP, TPP, PP) was added, to a tube labelled "B" containing H₂O (or thickening agent) such that the concentration of phosphate reagent was 5.0 wt % and H₂O (or thickening agent) was 0.55 wt % of stock.

Figure 3B:
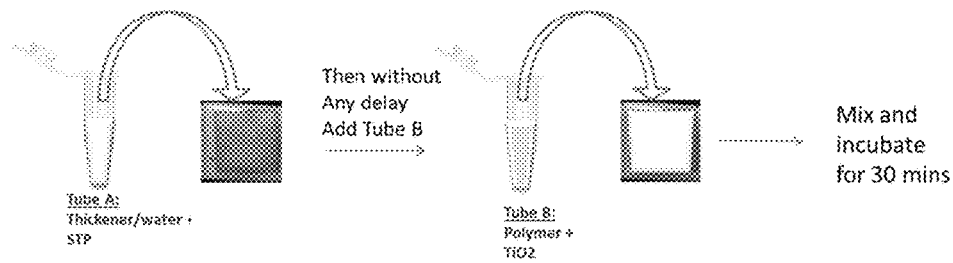
Figure 3B:
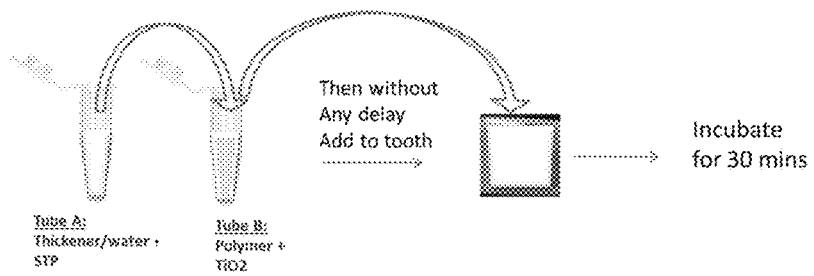

Whitening adhesives were applied to bovine tooth specimens previously stained with tea and coffee concentrates in sequential order (tube-A followed by tube-B, as depicted in FIG. 3B), and the mixture was incubated for 30 minutes, followed by rinsing with water and brushing for 10 seconds with an electric toothbrush.

The compositions of the polyelectrolyte mixtures are shown in Table 2.

TABLE 2

| Reagent | Stock Conc. | Amount Added | Final Conc. (wt %) |
| --- | --- | --- | --- |
| water/thickener | X% | 4 uL | .055X |
| TiO2 | 1% | 15 uL | 0.20 |
| STP | 25% | 15 uL | 5.0 |
| Polymer | 14% | 4 uL | 0.75 |
| Total | | 75 uL | |

Figure 5:
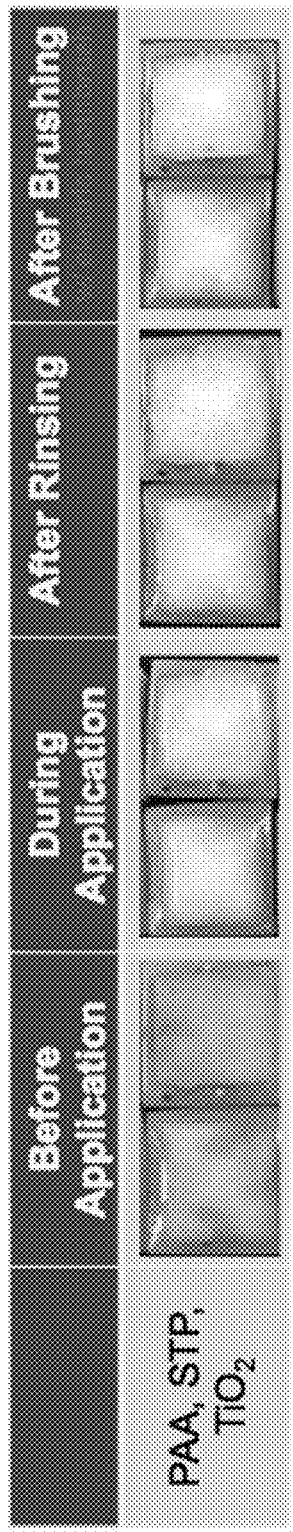
FIG. 5 contains photographs showing the appearance of whiter teeth following application of an exemplary whitening adhesive containing a conjugate of PAA, STP, and $TiO_2$, as described in exemplary procedure FIG. 3B.

As shown in FIG. 5, after application of a whitening adhesive containing PAA, STP, and TiO₂ the teeth appeared whiter, even after brushing.

Example 3: Polyelectrolyte Adhesive with TiO₂

Preparations of polyelectrolyte whitening adhesives containing PAA, STP, and TiO₂ were prepared as described below.

To prepare a whitening adhesive, 1 wt % TiO₂ was added to a solution of 14 wt % PAA adjusted to about pH 8, such that the whitening agent concentration was 0.2 wt % and polymer was 0.75 wt % in a tube labeled as "A". A 25 wt % phosphate reagent (e.g., STP) was added, to a tube labeled "B" containing H₂O such that the concentration of STP reagent was 5.0 wt % and H₂O was 0.55 wt % of stock.

Whitening adhesives were applied to bovine tooth specimens, previously stained with tea and coffee concentrates, in sequential order (tube-A followed by tube-B as depicted in FIG. 3B) and the mixture was incubated for 30 minutes, followed by rinsing with water and brushing for 10 seconds with an electric toothbrush.

As shown in FIG. 5, after application of a whitening adhesive containing PAA, STP, and TiO₂, the teeth appeared whiter, even after brushing Example 4: Polyelectrolyte Adhesive with TiO₂ and HA Preparations of polyelectrolyte whitening adhesives containing PAA, STP, and a combination of TiO₂ and HA were prepared as described below.

To prepare a whitening adhesive, 1 wt % TiO₂ and 5 wt % HA was added to a solution of 14 wt % PAA adjusted to about pH 8, such that the TiO₂ concentration was 0.1 wt %, HA concentration was 0.5 wt %, and polymer was 0.75 wt % in a tube labeled as "A". A 25 wt % phosphate reagent (e.g., STP) was added, to a tube labeled "B" containing H₂O such that the concentration of STP reagent was 5.0 wt % and H₂O was 0.55 wt % of stock.

Whitening adhesives were applied to bovine tooth specimens, previously stained with tea and coffee concentrates, in sequential order (tube-A followed by tube-B as depicted in FIG. 3B) and the mixture was incubated for 30 minutes, followed by rinsing with water and brushing for 10 seconds with an electric toothbrush.

Figure 6:
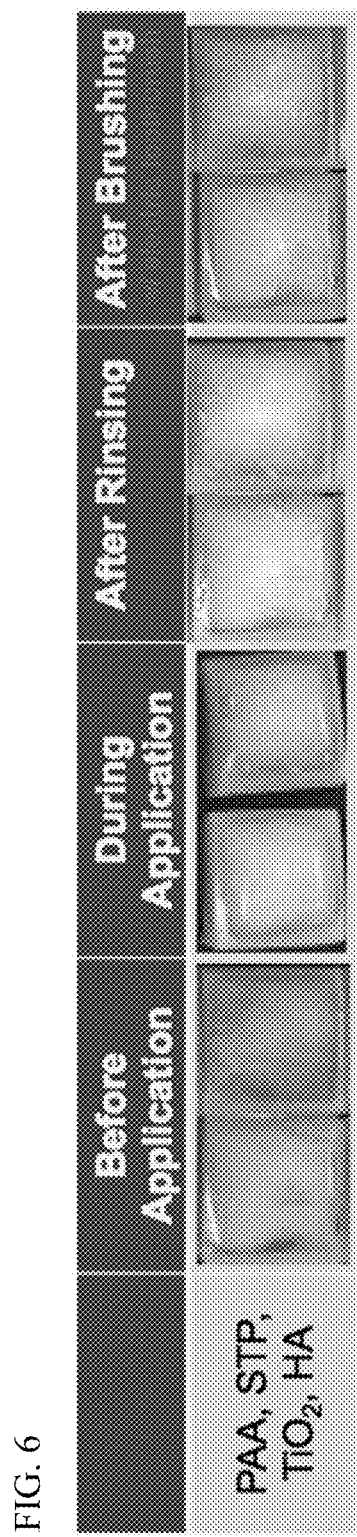
FIG. 6 contains photographs showing the appearance of whiter teeth following application of an exemplary whitening adhesive containing a conjugate of PAA, STP, and $TiO_2$, and hydroxyapatite (HA) either alone or as a part of the conjugate.

As shown in FIG. 6, after application of a whitening adhesive containing PAA, STP, TiO₂, and HA, the teeth appeared whiter, even after brushing.

Example 5: Polyelectrolyte Adhesive with TiO₂ and BFP

Preparations of polyelectrolyte whitening adhesives containing PAA, STP, and a combination of TiO₂ and BFP were prepared as described below.

To prepare a whitening adhesive, 1 wt % TiO₂ and 5 wt % BFP was added to a solution of 14% PAA adjusted to about pH 8, such that the TiO₂ concentration was 0.1 wt %, BFP concentration was 0.5 wt %, and polymer was 0.75 wt % in a tube labeled as "A". A 25 wt % phosphate reagent (e.g., STP) was added, to a tube labeled "B" containing H₂O such that the concentration of STP reagent was 5.0 wt % and H₂O was 0.55 wt % of stock.

Whitening adhesives were applied to bovine tooth specimens, previously stained with tea and coffee concentrates, in sequential order (tube-A followed by tube-B as depicted in FIG. 3B) and the mixture was incubated for 30 minutes, followed by rinsing with water and brushing for 10 seconds with an electric toothbrush.

Figure 7:
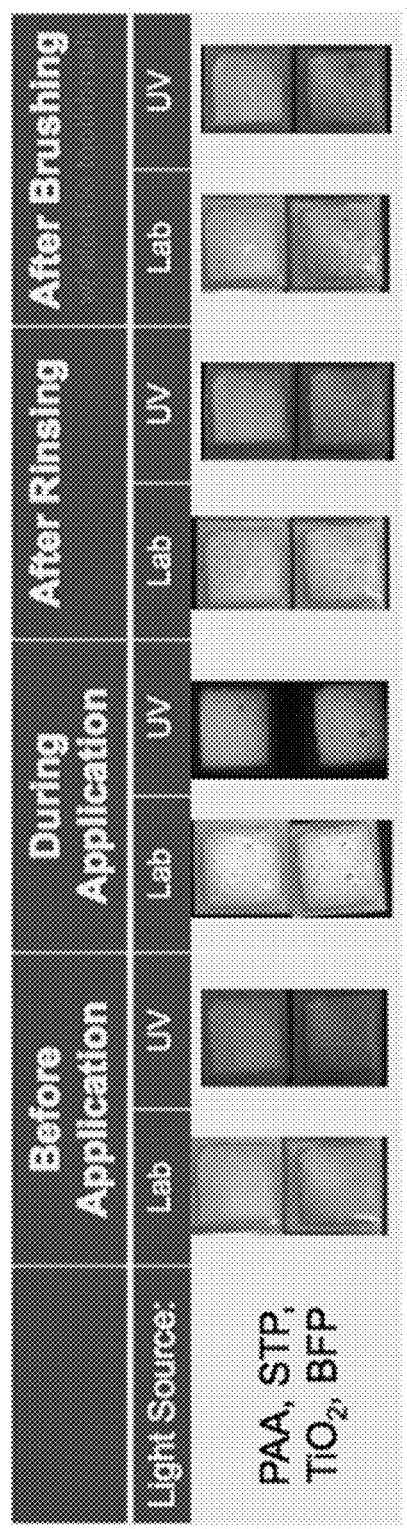
FIG. 7 contains photographs showing the appearance of whiter teeth following application of an exemplary whitening adhesive containing a conjugate of PAA, STP, and $TiO_2$ and blue fluorescent protein (BFP), either alone or as part of the conjugate.

As shown in FIG. 7, after application of a whitening adhesive containing PAA, STP, TiO₂, and BFP, the teeth appeared whiter, even after brushing.

Example 6: Polyelectrolyte Adhesive with TiO₂ and ZnO

Preparations of polyelectrolyte whitening adhesives containing PAA, STP, and a combination of TiO₂ and ZnO were prepared as described below.

To prepare a whitening adhesive, 1 wt % TiO₂ and 5 wt % ZnO was added to a solution of 14% PAA adjusted to about pH 8, such that the TiO₂ concentration was 0.1 wt %, ZnO concentration was 0.5 wt %, and polymer was 0.75 wt % in a tube labeled as "A". A 25 wt % phosphate reagent (e.g., STP) was added, to a tube labeled "B" containing H₂O such that the concentration of STP reagent was 5.0 wt % and H₂O was 0.55 wt % of stock.

Whitening adhesives were applied to bovine tooth specimens, previously stained with tea and coffee concentrates, in sequential order (tube-A followed by tube-B as depicted in FIG. 3B) and the mixture was incubated for 30 minutes, followed by rinsing with water and brushing for 10 seconds with an electric toothbrush.

Figure 8:
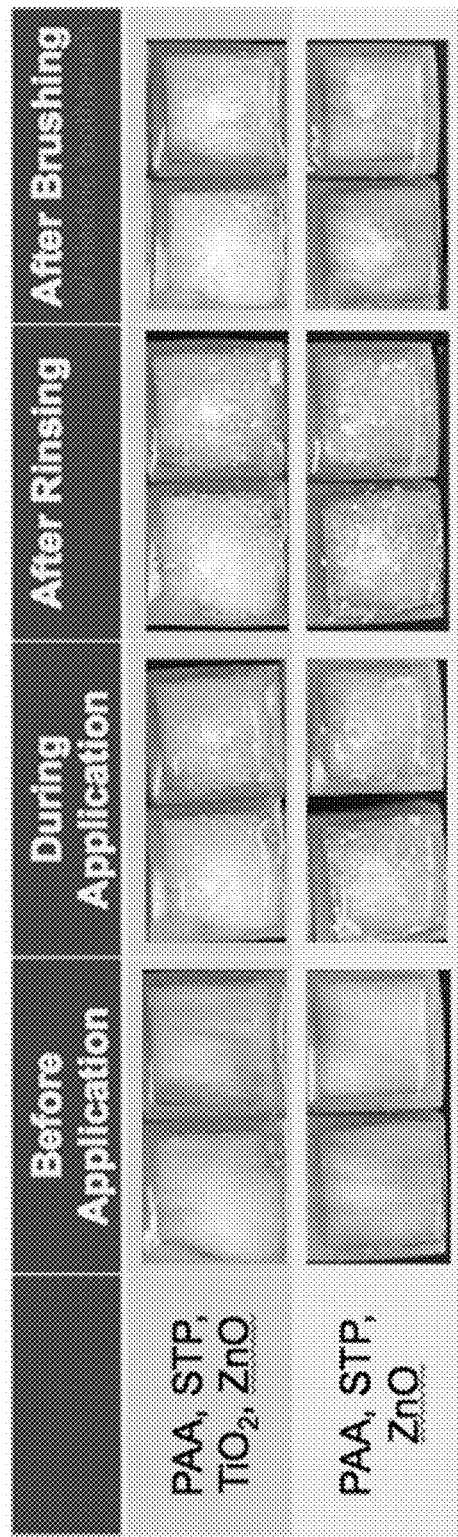
FIG. 8 contains photographs showing the appearance of whiter teeth following application of an exemplary whitening adhesive containing a conjugate of PAA, STP, and $TiO_2$ and ZnO (top panel) or an exemplary whitening adhesive containing a conjugate of PAA, STP, and ZnO (bottom panel).

As shown in FIG. 8 (top panel), after application of a whitening adhesive containing PAA, STP, TiO₂, and ZnO, the teeth appeared whiter, even after brushing.

Example 7: Polyelectrolyte Adhesive with ZnO

Preparations of polyelectrolyte whitening adhesives containing PAA, STP, and ZnO were prepared as described below.

To prepare a whitening adhesive, 5 wt % ZnO was added to a solution of 14 wt % PAA adjusted to about pH 8, such that the ZnO concentration was 1 wt %, and polymer was 0.75 wt % in a tube labeled as "A". A 25 wt % phosphate reagent (e.g., STP) was added, to a tube labeled "B" containing H₂O such that the concentration of STP reagent was 5.0 wt % and H₂O was 0.55 wt % of stock.

Whitening adhesives were applied to bovine tooth specimens, previously stained with tea and coffee concentrates, in sequential order (tube-A followed by tube-B as depicted in FIG. 3B) and the mixture was incubated for 30 minutes, followed by rinsing with water and brushing for 10 seconds with an electric toothbrush.

As shown in FIG. 8 (bottom Panel), after application of a whitening adhesive containing PAA, STP, and ZnO, the teeth appeared whiter, even after brushing.

Example 8: Polyelectrolyte Adhesive with STP or SHMP or PP or TPP

To prepare a whitening adhesive, 1 wt % whitening agent (e.g., titanium dioxide and/or zinc oxide optionally containing hydroxyapatite, blue fluorescent protein, silicon dioxide, bioactive glass or others) was added to water and/or a thickening agent (e.g., polyvinylpyrrolidone such as Kollidon K90F, Cellulose Gum) containing the tooth specimens incubated for 5 minutes, followed by addition of 20 wt % polymer (e.g., PAA, PAS-92, PAA-D41 adjusted to pH 7 to 9). A 25 wt % phosphate reagent (e.g., STP, SHMP, TPP, PP) was added, and the mixture was incubated for 30 minutes, followed by rinsing with water and brushing for 10 seconds with an electric toothbrush. A picture depicting the scheme of this preparation method is shown in FIG. 3A.

The composition of the polyelectrolyte mixture is shown in Table 3.

TABLE 3

| Reagent | Stock Conc. (%) | Amount Added (mL) | Final Conc. (Cf, Wt %) |
|---|---|---|---|
| water/Thickening agent /1x PBS | 1 | 9.25 | 0.740 |
| TiO2 | 1 | 1 | 0.080 |
| STP or SHMP or PP or TPP | 25 | 1 | 2.000 |
| Polymer | 20 | 1.25 | 2.000 |
| Total | | 12.5 | |

Figure 9A:
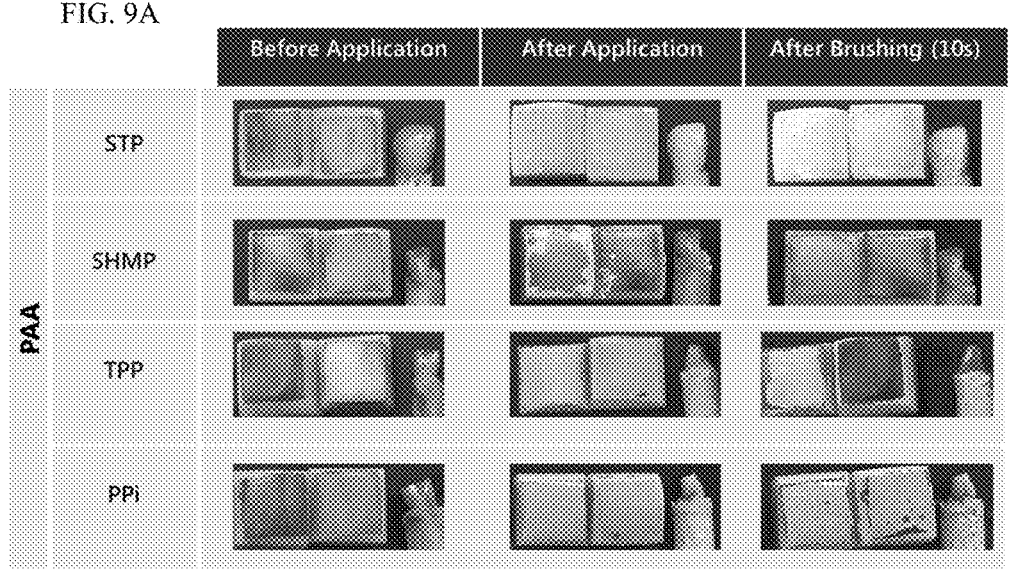
FIGS. 9A and 9B contain photographs showing the appearance of whiter teeth following application of an exemplary whitening adhesive containing a conjugate of a polyamine, a polyphosphate, and a whitening agent.
Figure 9B:
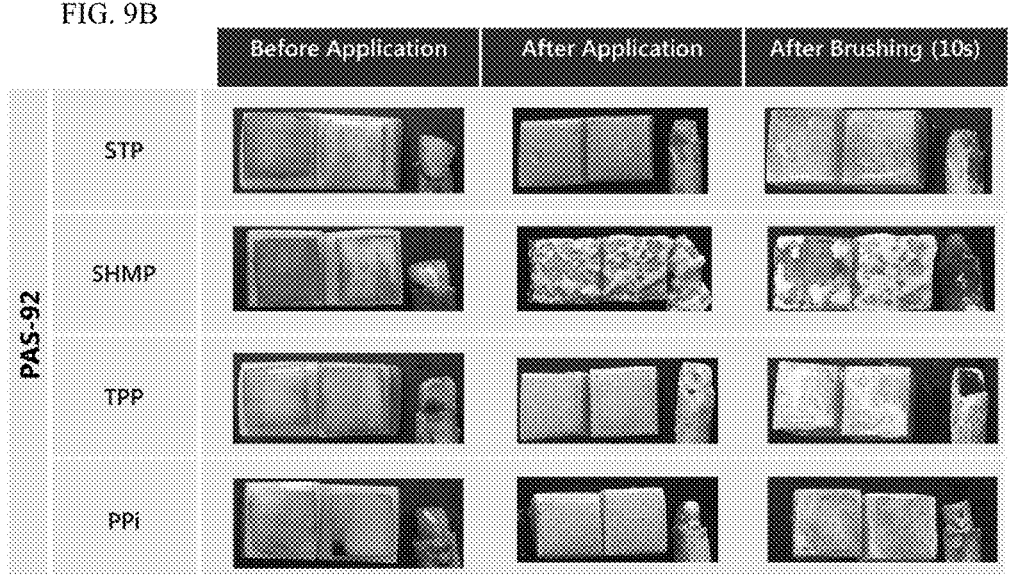

As shown in FIGS. 9A and 9B, after application of a whitening adhesive obtained using various polyanions (or phosphate reagents like STP or SHMP or TPP or PP) with PAA, and TiO₂, the teeth appeared whiter, even after brushing to various degree (FIG. 9A) and the same was true when performed with polymer PAS-92 (FIG. 9B).

OTHER EMBODIMENTS

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:
1. A whitening adhesive for coating teeth comprising a polyamine, a polyphosphate, and a whitening agent and having the ability to interact with or bind to a tooth, a tooth component, or an inorganic dental material, wherein said whitening agent of said whitening adhesive provides teeth with a white appearance when said whitening adhesive is adhered as a coating to said tooth, said tooth component, or said inorganic dental material, wherein said polyamine comprises

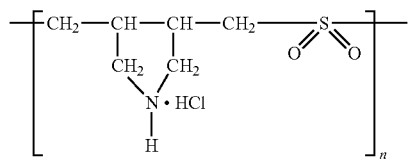

or

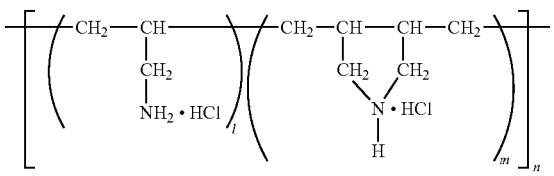

2. The whitening adhesive of claim 1, wherein said polyamine is

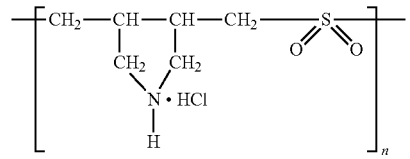

3. The whitening adhesive of claim 1, wherein said polyamine is

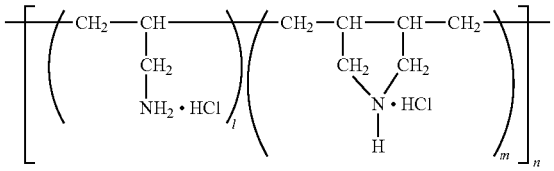

4. The whitening adhesive of claim 1, wherein said polyphosphate is selected from the group consisting of sodium hexametaphosphate, sodium trimetaphosphate, sodium tripolyphosphate, and sodium pyrophosphate.

5. The whitening adhesive of claim 1, wherein said polyphosphate is a cyclic polyphosphate, a linear polyphosphate, a potassium salt of a polyphosphate, or a sodium phosphate salt of a polyphosphate.

6. The whitening adhesive of claim 1, wherein said polyphosphate is a potassium salt of a polyphosphate.

7. The whitening adhesive of claim 1, wherein said polyphosphate is a sodium phosphate salt of a polyphosphate.

8. The whitening adhesive of claim 1, wherein said whitening agent comprises at least one of titanium dioxide, hydroxyapatite, silicon dioxide, zinc oxide, bioactive glass, and blue fluorescent protein.

9. The whitening adhesive of claim 1, wherein said whitening agent is titanium dioxide.

10. The whitening adhesive of claim 1, wherein said whitening agent is silicon dioxide.

11. The whitening adhesive of claim 1, wherein said whitening agent is zinc oxide.

12. A method for altering an appearance of teeth, said method comprising applying to teeth a polyamine, a polyphosphate, and a whitening agent, to form a whitening adhesive in the form of a coating on a surface of said teeth, wherein whitening agent of said whitening adhesive alters said appearance of said teeth, wherein said polyamine comprises

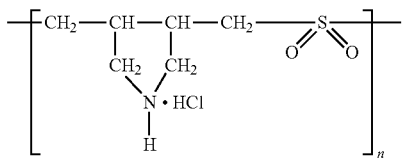

or

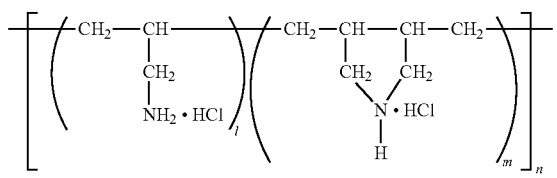

13. The method of claim 12, wherein said teeth are human teeth.

14. The method of claim 12, wherein said method comprises altering said appearance of said teeth such that said teeth appear whiter.

15. The method of claim 12, wherein said polyamine is

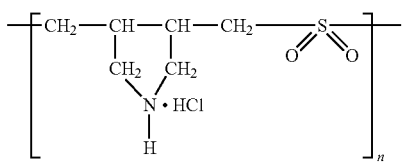

16. The method of claim 12, wherein said polyamine is

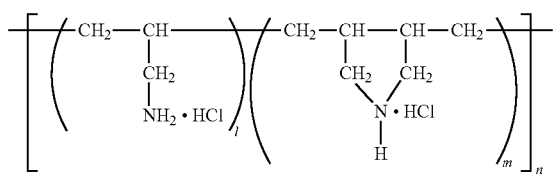

17. The method of claim 12, wherein said polyphosphate is selected from the group consisting of sodium hexametaphosphate, sodium trimetaphosphate, sodium tripolyphosphate, and sodium pyrophosphate.

18. The method of claim 12, wherein said polyphosphate is a cyclic polyphosphate, a linear polyphosphate, a potassium salt of a polyphosphate, or a sodium phosphate salt of a polyphosphate.

19. The method of claim 12, wherein said polyphosphate is a potassium salt of a polyphosphate.

20. The method of claim 12, wherein said polyphosphate is a sodium phosphate salt of a polyphosphate.

21. The method of claim 12, wherein said whitening agent comprises at least one of titanium dioxide, hydroxyapatite, silicon dioxide, zinc oxide, bioactive glass, and blue fluorescent protein.

22. The method of claim 12, wherein said whitening agent is titanium dioxide.

23. The method of claim 12, wherein said whitening agent is silicon dioxide.

24. The method of claim 12, wherein said whitening agent is zinc oxide.

25. The method of claim 12, wherein said applying step occurs in the presence of saliva.

26. A whitening adhesive for coating teeth comprising a polyamine, a polyphosphate, and a whitening agent and having the ability to interact with or bind to a tooth, a tooth component, or an inorganic dental material, wherein whitening agent of said whitening adhesive provides teeth with a white appearance when said whitening adhesive is adhered as a coating to said tooth, said tooth component, or said inorganic dental material, wherein said polyamine comprises from about 0.1 wt % to about 15 wt % of said whitening adhesive, wherein said polyphosphate comprises from about 5 wt % to about 60 wt % of said whitening adhesive, and wherein said whitening agent comprises from about 5 wt % to about 45 wt % of said whitening adhesive, and wherein said polyamine comprises

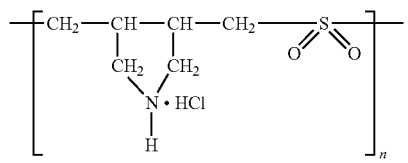

or

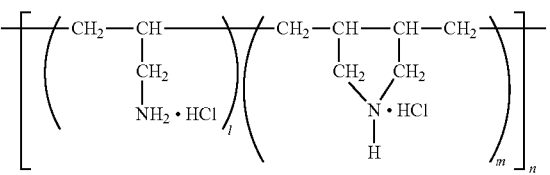

27. The whitening adhesive of claim 26, wherein said polyamine is

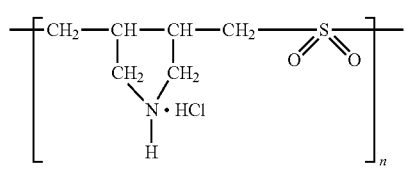

28. The whitening adhesive of claim 26, wherein said polyamine is $$\left[\left(\begin{array}{c}CH_2-CH\\|\\CH_2\\|\\NH_2\cdot HCl\end{array}\right)_l\left(\begin{array}{c}CH_2-CH-CH-CH_2\\|\quad\quad|\\CH_2\quad CH_2\\\diagdown\quad\diagup\\N\cdot HCl\\|\\H\end{array}\right)_m\right]_n$$

29. The whitening adhesive of claim 26, wherein said polyphosphate is selected from the group consisting of sodium hexametaphosphate, sodium trimetaphosphate, sodium tripolyphosphate, and sodium pyrophosphate.

30. The whitening adhesive of claim 26, wherein said polyphosphate is a cyclic polyphosphate, a linear polyphosphate, a potassium salt of a polyphosphate, or a sodium phosphate salt of a polyphosphate.

31. The whitening adhesive of claim 26, wherein said polyphosphate is a potassium salt of a polyphosphate.

32. The whitening adhesive of claim 26, wherein said polyphosphate is a sodium phosphate salt of a polyphosphate.

33. The whitening adhesive of claim 26, wherein said whitening agent comprises at least one of titanium dioxide, hydroxyapatite, silicon dioxide, zinc oxide, bioactive glass, and blue fluorescent protein.

34. The whitening adhesive of claim 26, wherein said whitening agent is titanium dioxide.

35. The whitening adhesive of claim 26, wherein said whitening agent is silicon dioxide.

36. The whitening adhesive of claim 26, wherein said whitening agent is zinc oxide.

37. A method for altering an appearance of teeth, wherein said method comprises applying to teeth a whitening adhesive in the form of a coating, wherein said whitening adhesive comprises a polyamine, a polyphosphate, and a whitening agent and has the ability to interact with or bind to a tooth, a tooth component, or an inorganic dental material, wherein whitening agent of said whitening adhesive provides teeth with a white appearance when said whitening adhesive is adhered to said tooth, said tooth component, or said inorganic dental material, wherein said polyamine comprises from about 0.1 wt % to about 15 wt % of said whitening adhesive, wherein said polyphosphate comprises from about 5 wt % to about 60 wt % of said whitening adhesive, and wherein said whitening agent comprises from about 5 wt % to about 45 wt % of said whitening adhesive, wherein said polyamine comprises $$\left[\begin{array}{c}CH_2-CH-CH-CH_2\\|\quad\quad|\\CH_2\quad CH_2\\\diagdown\quad\diagup\\N\cdot HCl\\|\\H\end{array}\quad\begin{array}{c}S\\\diagup\diagdown\\O\quad O\end{array}\right]_n$$

or $$\left[\left(\begin{array}{c}CH_2-CH\\|\\CH_2\\|\\NH_2\cdot HCl\end{array}\right)_l\left(\begin{array}{c}CH_2-CH-CH-CH_2\\|\quad\quad|\\CH_2\quad CH_2\\\diagdown\quad\diagup\\N\cdot HCl\\|\\H\end{array}\right)_m\right]_n$$

38. The method of claim 37, wherein said teeth are human teeth.

39. The method of claim 37, wherein said method comprises altering said appearance of said teeth such that said teeth appear whiter.

40. The method of claim 37, wherein said polyamine is $$\left[\begin{array}{c}CH_2-CH-CH-CH_2\\|\quad\quad|\\CH_2\quad CH_2\\\diagdown\quad\diagup\\N\cdot HCl\\|\\H\end{array}\quad\begin{array}{c}S\\\diagup\diagdown\\O\quad O\end{array}\right]_n$$

41. The method of claim 37, wherein said polyamine is $$\left[\left(\begin{array}{c}CH_2-CH\\|\\CH_2\\|\\NH_2\cdot HCl\end{array}\right)_l\left(\begin{array}{c}CH_2-CH-CH-CH_2\\|\quad\quad|\\CH_2\quad CH_2\\\diagdown\quad\diagup\\N\cdot HCl\\|\\H\end{array}\right)_m\right]_n$$

42. The method of claim 37, wherein said polyphosphate is selected from the group consisting of sodium hexametaphosphate, sodium trimetaphosphate, sodium tripolyphosphate, and sodium pyrophosphate.

43. The method of claim 37, wherein said polyphosphate is a cyclic polyphosphate, a linear polyphosphate, a potassium salt of a polyphosphate, or a sodium phosphate salt of a polyphosphate.

44. The method of claim 37, wherein said polyphosphate is a potassium salt of a polyphosphate.

45. The method of claim 37, wherein said polyphosphate is a sodium phosphate salt of a polyphosphate.

46. The method of claim 37, wherein said whitening agent comprises at least one of titanium dioxide, hydroxyapatite, silicon dioxide, zinc oxide, bioactive glass, and blue fluorescent protein.

47. The method of claim 37, wherein said whitening agent is titanium dioxide.

48. The method of claim 37, wherein said whitening agent is silicon dioxide.

49. The method of claim 37, wherein said whitening agent is zinc oxide.

50. The method of claim 37, wherein said applying step occurs in the presence of saliva.

\* \* \* \* \*